United States Patent [19]
Irikura et al.

[11] Patent Number: 4,788,320
[45] Date of Patent: Nov. 29, 1988

[54] BENZOYLACETIC ACID ESTER DERIVATIVES AND PROCESS FOR THEIR PREPARATIONS

[75] Inventors: Tsutomu Irikura, Tokyo; Seigo Suzue, Kuki; Satoshi Murayama, Tochigi; Keiji Hirai, Kuki; Takayoshi Ishizaki, Saitama, all of Japan

[73] Assignee: Kyorin Pharmaceutical Co., Ltd., Tokyo, Japan

[21] Appl. No.: 4,043

[22] Filed: Jan. 16, 1987

[30] Foreign Application Priority Data

Jan. 20, 1986 [JP] Japan .................................. 61-9649
Dec. 1, 1986 [JP] Japan ................................ 61-286524

[51] Int. Cl.$^4$ ............................................ C07C 69/76
[52] U.S. Cl. ................................... 560/54; 560/51
[58] Field of Search ................................. 560/51, 54

[56] References Cited

U.S. PATENT DOCUMENTS 4,611,080 9/1986 Grohe .................................. 560/51

FOREIGN PATENT DOCUMENTS 3420743 12/1985 Fed. Rep. of Germany ........ 560/51

OTHER PUBLICATIONS

CA 104(21):186446U Germ. Offen. DE 3420743A1 Dec. 5, 1985.

Primary Examiner—Paul J. Killos
Attorney, Agent, or Firm—Oblon, Fisher, Spivak, McClelland & Maier

[57] ABSTRACT

The present invention is concerned with certain novel benzoylacetic acid ester derivatives (I) which are useful as a intermediates for synthesis of antibacterial agests.

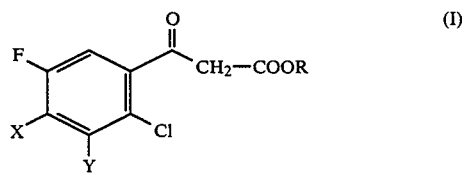

wherein R is a lower alkyl group, X is a halogen atom and Y is a chlorine or bromine atom.

5 Claims, No Drawings

BENZOYLACETIC ACID ESTER DERIVATIVES AND PROCESS FOR THEIR PREPARATIONS

DETAILED DESCRIPTION OF THE INVENTION

The present invention is concerned with certain novel benzoylacetic acid ester derivatives of the following formula (I) which are useful as a intermediates for the synthesis of medicinal compounds, especially antibacterial agents, and with a process for their preparation.

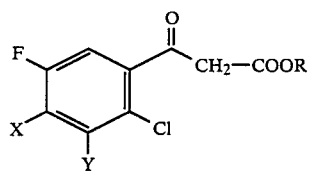

wherein R is a lower alkyl group, X is a halogen atom and Y is a chlorine or bromine atom.

We have found that the introduction of a chlorine atom or bromine atom at the 8-position in the antibacterial quinolonecarboxylic acid analogue gives rise to enhanced activity.

Thus, 8-chloro- or 8-bromo-1-cyclopropyl-6-fluoro-1,4-dihydro-7-substituted amino-4-oxo-3-quinolinecarboxylic acid derivatives were found to be useful antibacterial agents.

The compounds of the present invention may be prepared by the condensation of a benzoyl chloride derivatives of the formula (II) with a malonic acid dialkyl ester in the presence of magnesium alcoholate to give benzoylmalonic acid ester (III) and then decarboxylation of the ester (III) by treatment with aqueous acid solution.

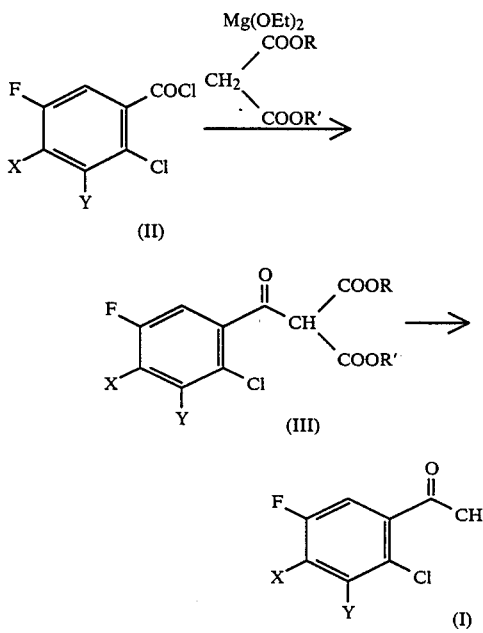

wherein R and R' are each independently a lower alkyl group, X is a halogen atom and Y is a chlorine or bromine atom.

The condensation reaction may be carried out by treating the two reactants in an innert solvent such as ether, toluene and the like at a temperature of −50° to 50° C., preferably −20° to room temperature. The above condition enables the reaction to be completed in 10 minutes to 20 hours.

The decarboxylation reaction may be carried out by refluxing the ester (III) in an aqueous solution in the presence of catalytic amount of p-toluenesulfonic acid for 30 minutes to 20 hours.

The compound of the fomrula (I) of the present invention may be converted by the following scheme to the novel valuable antibacterial agents.

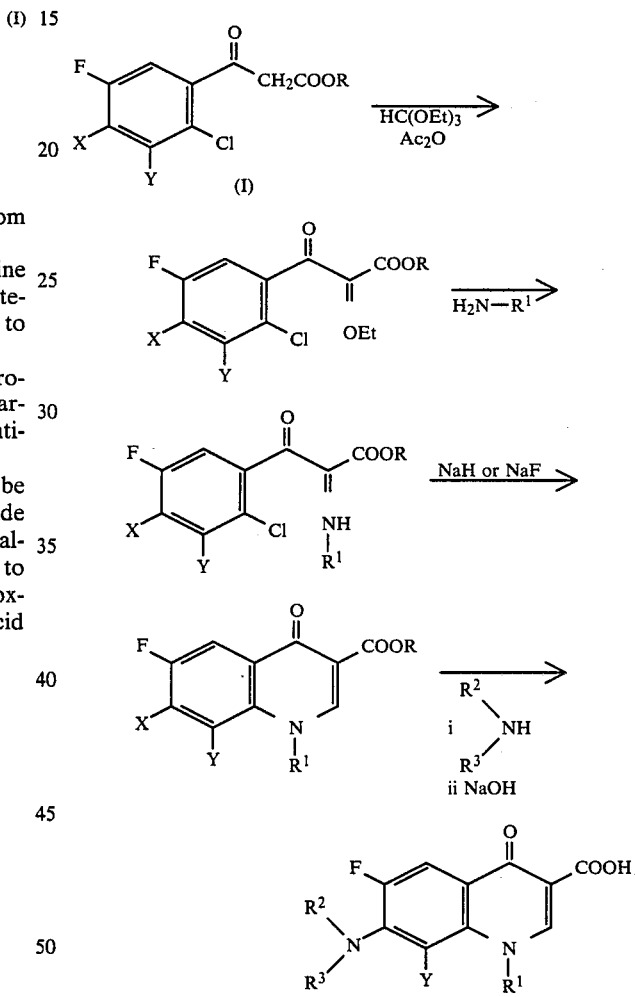

The following examples will further illustrate the invention without, however, limiting it thereto.

Example 1

Diethyl 2-(2,3-dichloro-4,5-difluorobenzoyl)-malonate

Magnesium turnings (0.77 g) and carbon tetrachloride (0.4 ml) was added to absolute ethanol (5.3 ml). To the stirring suspension was added a solution of diethyl malonate (4.89 g) and absolute ethanol (8.5 ml) in toluene (21.3 ml) dropwise during 40 minutes at 20° to 40° C. The mixture was stirred at 50° to 60° C. for 2 hours, and then cooled in an acetone-dry ice bath. A solution of 2,3-dichloro-4,5-difluorobenzoyl chloride (6.00 g) in anhydrous toluene (7.1 ml) was added dropwise to the resulting solution at −18° to −13° C. during 10 minutes. The mixture was warmed gradually to room temperature during 2 hours and then mixed with ice water (17 ml) containing concentrated sulfuric acid (1.1 ml). The resulting organic layer was collected and the water layer was extracted with toluene. The combined organic layer was washed with water, dried over anhydrous sodium sulfate and then concentrated to give the title compound (9.68 g) as pale yellow oil.

EXAMPLE 2

Ethyl 2-(2,3-dichloro-4,5-difluorobenzoyl)acetate

To an emulsion of diethyl 2-(2,3-dichloro-4,5-difluorobenzoyl)malonate (9.71 g) in water (11.2 ml) was added p-toluenesulfonic acid (11.2 mg) and refluxed for 3 hours with stirring vigorously. After cooling, the reaction mixture was extracted with dichloromethane. The organic layer was washed with 7% aqueous sodium carbonate solution and then with water successively, dried over anhydrous sodium sulfate and concentrated. The residue was recrystallized from n-hexane to give the title compound (4.24 g) as powdery crystals. mp 52°-53° C.

Analysis (%) for $C_{11}H_8Cl_2F_2O_3$, Calcd. (Found) C, 44.47 (44.59); H, 2.71 (2.65).

EAMPLE 3

Diethyl 2-(3-bromo-2-chloro-4,5-difluorobenzoyl)malonate

To the magnesium ethoxide (3.93 g) suspension was added a solution of diethyl malonate (4.65 g) in anhydrous toluene (30 ml) dropwise during 25 minutes at 20° to 25° C. The mixture was stirred at 50° to 60° C. for 3 hours, and then cooled in an acetone-dry ice bath. A solution of 3-bromo-2-chloro-4,5-difluorobenzoyl chloride (7.65 g) in anhydrous toluene (15 ml) was added dropwise to the resulting solution at $-16°$ to 0° C. during 25 minutes. The mixture was stirred for 2.5 hours below 0° C., then further stirred at room temperature for 40 minutes, and then mixed with ice water (15 ml) containing concentrated sulfuric acid (1 ml). The resulting organic layer was collected and the water layer was extracted with toluene. The combined organic layer was washed with water, dried over anhydrous sodium sulfate and then concentrated to give the title compound (11.44 g) as pale yellow oil.

EXAMPLE 4

Ethyl 2-(3-bromo-2-chloro-4,5-difluorobenzoyl)acetate

To an emulsion of diethyl 2-(3-bromo-2-chloro-4,5-difluorobenzoyl)malonate (11.44 g) in water (16 ml) was added p-toluenesulfonic acid (15 mg) and refluxed for 3 hours with stirring vigorously. After cooling, the reaction mixture was extracted with dichloromethane. The organic layer was washed with water, dried over anhydrous sodium sulfate and concentrated. The residue was purified by silica gel chromatography eluting with dichloromethane-n-hexane (1:1) to give the title compound (4.56 g), mp 47°-51° C.

Analysis (%) for $C_{11}8BrClF_2O_3$, Calcd. (Found): C, 38.68 (37.94); H, 2.36 (2.19).

In example 1 and 3, the starting materials are synthesized by following process.

REFERENCE EXAMPLE 1

N-(3,4-difluorophenyl)acetamide

To 3,4-difluoroaniline (28.2 g) was added acetic anhydride (30 ml) slowly. After allowed to stand for 30 minutes, the reaction mixture was poured into ice water (100 ml). The resulting precipitate was collected by filtration and washed with water sufficiently to give the title compound (34.7 g) as colorless needles, mp 127°-127.5° C.

Analysis (%) for $C_8H_7F_2NO$, Calcd. (Found): C, 56.14 (56.15); H, 4.12 (4.06); N, 8.18 (8.00).

REFERENCE EXAMPLE 2

4,5-Difluoro-2-nitroaniline

To a solution of N-(3,4-difluorophenyl)acetamide (48 g) in concentrated sulfuric acid (140 ml) was added dropwise concentrated nitric acid (d 1.42, 56 ml) at $-1°$ to 3° C. during 50 minutes with stirring in an ice-salt bath. After stirring for 1.5 hours at 3° to 16° C., the reaction mixture was poured into ice water (560 ml). The resulting precipitate was collected by filtration, washed with chilled water sufficiently to give N-(4,5-difluoro-2-nitrophenyl)acetamide (55.3 g).

A solution of N-(4,5-difluoro-2-nitrophenyl)acetamide (70 g) in concentrated hydrochloric acid (110 ml) and ethanol (440 ml) was refluxed for 2 hours. The reaction mixture was poured into ice water (1.5 liter) and the resulting precipitate was collected by filtration and washed with chilled water sufficiently to give the title compound (53.2 g) as yellow prisms, mp 109°-109.5° C.

Analysis (%) for $C_6H_4F_2N_2O_2$, Calcd. (Found): C, 41.39 (41.29); H, 2.32 (2.31); N, 16.09 (15.96).

REFERENCE EXAMPLE 3

2-Chloro-3,4-difluoro-6-nitroaniline

Into a solution of 4,5-difluoro-2-nitroaniline (20 g) in acetic acid (200 ml) was boubled chlorine gas at 13° to 15° C. during 45 minutes. The reaction mixture was poured into ice water (500 ml) and extracted with dichloromethane. The organic layer was washed with 6% aqueous sodium carbonate and with water successively, dried over anhydrous sodium sulfate and then concentrated. The residue was purified with silica gel chromatography eluting with dichloromethane-n-hexane (1:4) and further recrystallized from hexane to give the title compound (2.91 g) as yellow needles, mp 86°-88° C.

Analysis (%) for $C_6H_3ClF_2N_2O_2$, Calcd. (Found): C, 34.56 (34.58); H, 1.45 (1.37); N, 13.43 (13.41).

REFERENCE EXAMPLE 4

2,3-Dichloro-4,5-difluoronitrobenzene

To a mixture of anhydrous cupric chloride (2.2 g) and 2-chloro-3,4-difluoro-6-nitroaniline (2.63 g) in anhydrous acetonitrile (20 ml) was added t-butylnitrite (2.0 g) dropwise at 46° to 55° C. during 9 minutes. After stirring for 13 minutes at the same temperature, the reaction mixture was poured into chilled 10 diluted hydrochloric acid (20 ml) and extracted with benzene. The organic layer was washed with diluted hydrochloric acid and with water successivly, dried over anhydrous sodium sulfate and concentrated. The resulting residue was purified by silica gel chromatography eluting with dichloromethane-n-hexane (1:5) to give the title compound (2.47 g), as yellow oil.

NMR ($\delta$ in $CDCl_3$), 7.75 (dd, J=7.0, 8.8 Hz).

REFERENCE EXAMPLE 5

2,3-Dichloro-4,5-difluoroaniline

To a suspension of iron powder (1.9 g) in water (3 ml), with vigorous stirring at 50° to 60° C., was added concentrated hydrochloric acid (0.4 ml) slowly. After mixed with ethanol (7 ml), 2,3-dichloro-4,5-difluoronitrobenzene (2.47 g) in ethanol (3 ml) was added dropwise to the suspension at 54° to 66° C. during 20 minutes. After stirring for 4 hours at the same temperature, the hot reaction mixture mixed with benzene was filtered and the insoluble materials were washed with hot ethanol (5 ml) and with benzene (20 ml) successively. The filtrate and washings were combined and mixed with ice water. The resulting organic layer was collected, washed with water, dried over anhydrous sodium sulfate and then concentrated. The resulting residue was purified by silica gel chromatography eluting with dichloromethane-n-hexane (1:3) to give the title compound (0.89 g) as colorless needles, mp 94°–97.5° C.

NMR ($\delta$ in $CDCl_3$), 6.52 (dd, J=7.0, 11.4 Hz).

REFERENCE EXAMPLE 6

2,3-Dichloro-4,5-difluorobenzenediazonium tetrafluoroborate

To a suspension of 2,3-dichloro-4,5-difluoroaniline (0.88 g) in 42% fluoroboric acid (10 ml) with stirring vigorously was added sodium nitrite (0.43 g) in water (1 ml) at −15° to 0° C. for 14 minutes. After stirred for 3 hours at the same temperature, the resulting precipitate was collected by filtration, washed with 42% fluoroboric acid and then with ether to give the title compound (0.66 g) as white powdery crystals, mp 211° C. (decompd.).

IR (KBr, $cm^{-1}$), 2300 (CN).

REFERENCE EXAMPLE 7

2,3-Dichloro-4,5-difluorobenzonitrile 2,3-Dichloro-4,5-difluorobenzenediazonium tetrafluoroborate (0.65 g) was added portionwise during 10 minutes to a solution of cuprous cyanide (0.4 g), potassium cyanide (0.58 g) and sodium carbonate (0.12 g) in water (10 ml) with stirring vigorously at room temperature. After the mixture was stirred for 2.8 hours, benzene (20 ml) was added to the suspension and then the mixture was stirred for 15 minutes. The insoluble materials were collected by filtration, and washed with benzene. The filtrate and washings were combined and washed with water, dried over anhydrous sodium sulfate and then concentrated. The resulting residue was purified by silica gel chromatography eluting with dichloromethane-n-hexane (1:3) to give the title compound (0.15 g), mp 46.5°–49.5° C.

NMR ($\delta$ in $CDCl_3$), 7.49 (dd, J=7.3, 8.6 Hz).
IR (KBr, $cm^{-1}$), 2260 (CN).
Mass m/e; 207 (M+), 209 (M++2), 211 (M+4), Calcd. MW. 207.99 for $C_7HCl_2F_2N$.

REFERENCE EXAMPLE 8

2,3-Dichloro-4,5-difluorobenzamide

A solution of 2,3-dichloro-4,5-difluorobenzonitrile (1.0 g) in concentrated sulfuric acid (2.5 ml) was stirred at 90° to 100° C. for 30 minutes and then cooled. The residue was poured into ice water and the resulting precipitate was collected by filtration and recrystallized from benzene to give the title compound (0.51 g) as colorless needles, mp 153°–155° C.

Analysis (%) for $C_7H_3Cl_2F_2NO$, Calcd. (Found): C, 37.20 (37.24); H, 1.34 (1.33); N, 6.20 (6.15).

REFERENCE EXAMPLE 9

2,3-Dichloro-4,5-difluorobenzoic acid

A mixture of 2,3-dichloro-4,5-difluorobenzamide (0.5 g) and 18N-sulfuric acid (2.5 ml) was stirred at 125° to 135° C. for 9 hours, and then poured into ice water. After standing overnight, the resulting precipitate was collected by filtration and recrystallized from hexane-benzene to give the title compound (0.3 g) as colorless prisms.

Analysis (%) for $C_7H_2Cl_2F_2O_2$, Calcd. (Found) C, 37.04 (37.23); H, 0.89 (0.93).

REFERENCE EXAMPLE 10

2,3-Dichloro-4,5-difluorobenzoyl chloride

A solution of 2,3-dichloro-4,5-difluorobenzoic acid (9.3 g) and dimethylformamide (0.013 ml) in thionyl chloride (40 ml) was refluxed for 2.5 hours, and then concentrated. The resulting residue was purified by distillation in nitrogen atmosphere to give the title compound (8.7 g) as pale yellow oil, bp 123°–126° C./40 mmHg.

NMR ($\delta$ in $CDCl_3$), 7.89 (dd, J=7.5, 9.7 Hz)

REFERENCE EXAMPLE 11

2-Bromo-3,4-difluoro-6-nitroaniline

Into a solution of 4,5-difluoro-2-nitroaniline (3.7 g) in acetic acid (27 ml) was added bromine (6.8 g) dropwise at 50° 1 to 56° C. and stirred for 2.5 hours. The reaction mixture was poured into ice water (60 ml) and the resulting precipitate was collected by filtration and washed with water sufficiently to give the title compound (4.7 g) as yellow prisms, mp 105° C.

Analysis (%) for $C_6H_3BrF_2N_2O_2$, Calcd. (Found): C. 28.48 (28.62); H, 1.20 (1.15); N, 11.07 (11.00).

REFERENCE EXAMPLE 12

3-Bromo-2-chloro-4,5-difluoronitrobenzene

To a mixture of anhydrous cupric chloride (3.1 g) and 2-bromo-3,4-difluoro-6-nitroaniline (4.6 g) in anhydrous acetonitrile (30 ml) was added t-butylnitrite (2.8 g) dropwise at 51° to 56° C. during 5 minutes. After stirring for 8 minutes at the same temperature, the reaction mixture was poured into chilled 10% diluted hydrochloric acid (30 ml) and extracted with benzene. The organic layer was washed with diluted hydrochloric acid and with water successively, dried over anhydrous sodium sulfate and concentrated. The resulting residue was purified by silica gel chromatography eluting with dichloromethane-n-hexane (1:5) to give the title compound (4.0 g).

NMR ($\delta$ in $CDCl_3$), 7.79 (d, J=7.0, 8.8 Hz)

REFERENCE EXAMPLE 13

3-Bromo-2-chloro-4,5-difluoroaniline

To a suspension of iron powder (38.6 g) in water (40 ml), with stirring vigorously at 50° to 60° C., was slowly added concentrated hydrochloric acid (5 ml). After mixed with ethanol (100 ml), 3-bromo-2-chloro-4,5-difluoronitrobenzene (58.8 g) was added portionwise to the suspension at 60° to 75° C. during 30 minutes. After stirring for 70 minutes, the hot reaction mixture was filtered and the insoluble materials were washed with hot ethanol (30 ml) and with benzene (100 ml) successively. The filtrate and washings were combined and mixed with ice water. The resulting organic layer was washed with water, dried over anhydrous sodium sulfate and then concentrated. The resulting residue was purified by silica gel chromatography eluting with dichloromethane-n-hexane (1:1) to give the title compound (34.5 g) as light brown prisms, mp 83°–86° C.

REFERENCE EXAMPLE 14

3-Bromo-2-chloro-4,5-difluorobenzenediazonium tetrafluoroborate

To a suspension of 3-bromo-2-chloro-4,5-difluoroaniline (30.1 g) in 42% fluoroboric acid (180 ml) with stirring vigorously was added sodium nitrite (12 g) in water (30 ml) at −9° to 1° C. for 40 minutes. After stirred for 1.5 hours, the resulting precipitate was collected by filtration and washed with 42% fluoroboric acid and then with ether to give the title compound (35.6 g) as light yellow needles, mp 300° C.

IR (KBr, cm$^{-1}$); 2280 (—N≡N$^+$)

REFERENCE EXAMPLE 15

3-Bromo-2-chloro-4,5-difluorobenzonitrile

3-Bromo-2-chloro-4,5-difluorobenzenediazonium tetrafluoroborate (35.6 g) was added portionwise during 40 minutes to a solution of cuprous cyanide (18.67 g), potassium cyanide (27.14 g) and sodium carbonate (5.52 g) in water (200 ml) with stirring vigorously at room temperature. After the mixture was stirred for 4.5 hours, benzene (250 ml) was added to the suspension and then the mixture was stirred for 25 minutes. The insoluble materials were collected by filtration, and washed with benzene. The filtrate and washings were combined and washed with water, dried over anhydrous sodium sulfate and then concentrated. The resulting residue was purified by silica gel chromatography eluting with dichloromethane-n-hexane (1:3) and further recrystallized from n-hexane-dichloromethane to give the title compound (10.9 g) as light yellow needles, mp 71°–72.5° C.

Analysis (%) for C$_7$HBrClF$_2$N, Calcd. (Found): C, 33.31 (33.22); H, 0.40 (0.31); N, 5.55 (5.48).

REFERENCE EXAMPLE 16

3-Bromo-2-chloro-4,5-difluorobenzoic acid

A solution of 3-bromo-2-chloro-4,5-difluorobenzonitrile (9.8 g) in concentrated sulfuric acid (10 ml) was stirred at 100° C. for 35 minutes. After cooling, 18N sulfuric acid (50 ml) and water (10 ml) were added to the reaction mixture. The reaction mixture was stirred at 100° C. for 4 hours and then poured into ice water (300 ml). The resulting precipitate was collected by filtration, washed with water sufficiently and recrystallized from dichloromethane-n-hexane to give the title compound (9.24 g) as colorless prisms, mp 137.5°–139.5° C.

Analysis (%) for C$_7$H$_2$BrClF$_2$O$_2$, Calcd. (Found): C, 30.97 (30.96); H, 0.74 (0.71).

REFERENCE EXAMPLE 17

3-Bromo-2-chloro-4,5-difluorobenzoyl chloride

A solution of 3-bromo-2-chloro-4,5-difluorobenzoic acid (9.0 g) in thionyl chloride (33 ml) was refluxed for 2.5 hours, and then concentrated. The resulting residue was purified by distillation to give the title compound (8.8 g), bp 109° C./22 mmHg.

NMR (δ in CDCl$_3$), 7.93 (d, J=7.5, 9.7 Hz).

What is claimed is:

1. Benzoylacetic acid ester derivatives of the formula (I),

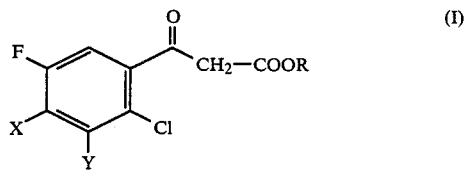

wherein R is a lower alkyl group, X is a halogen atom and Y is a chlorine or bromine atom.

2. The benzoylacetic acid ester of claim 1 which is ethyl 2-(2,3-dichloro-4,5-difluorobenzoyl) acetate.

3. The benzoylacetic acid ester of claim 1 which is ethyl 2-(3-bromo-2-chloro-4,5-difluorobenzoyl) acetate.

4. The benzoylacetic acid ester which is diethyl 2-(2,3-dichloro-4,5-difluorobenzoyl) malonate.

5. The benzoylacetic acid ester which is diethyl 2-(3-bromo-2-chloro-4,5-difluorobenzoyl) malonate.

* * * * *